(12) United States Patent
Gagnon

(10) Patent No.: US 9,442,050 B2
(45) Date of Patent: Sep. 13, 2016

(54) REDUCING PH EXCURSIONS IN ION EXCHANGE CHROMATOGRAPHY USING DISPLACING COUNTER IONS

(71) Applicant: Peter S. Gagnon, Singapore (SG)

(72) Inventor: Peter S. Gagnon, Singapore (SG)

(73) Assignee: BIO-RAD LABORATORIES, INC., Hercules, CA (US)

( * ) Notice: Subject to any disclaimer, the term of this patent is extended or adjusted under 35 U.S.C. 154(b) by 680 days.

(21) Appl. No.: 13/763,064

(22) Filed: Feb. 8, 2013

(65) Prior Publication Data

US 2013/0210164 A1    Aug. 15, 2013

Related U.S. Application Data

(60) Provisional application No. 61/598,706, filed on Feb. 14, 2012.

(51) Int. Cl.

| | | |
|---|---|---|
| *G01N 1/34* | (2006.01) | |
| *G01N 30/96* | (2006.01) | |
| *B01D 15/20* | (2006.01) | |
| *B01D 15/42* | (2006.01) | |
| *B01D 15/32* | (2006.01) | |
| *B01D 15/36* | (2006.01) | |
| *B01D 15/38* | (2006.01) | |

(52) U.S. Cl.
CPC ............... *G01N 1/34* (2013.01); *B01D 15/20* (2013.01); *B01D 15/422* (2013.01); *G01N 30/96* (2013.01); *B01D 15/327* (2013.01); *B01D 15/362* (2013.01); *B01D 15/363* (2013.01); *B01D 15/3847* (2013.01); *Y10T 436/25375* (2015.01)

(58) Field of Classification Search
CPC ........ G01N 1/34; G01N 30/96; G01N 30/50; B01D 15/20; B01D 15/422; B01D 15/327; B01D 15/363; B01D 15/3847; B01D 15/362; B01D 15/203; Y10T 436/25375
See application file for complete search history.

(56) References Cited

U.S. PATENT DOCUMENTS

| | | | |
|---|---|---|---|
| 7,101,982 B2 | 9/2006 | Ghose et al. | |
| 2003/0004094 A1* | 1/2003 | Ghose et al. | ............ 514/2 |
| 2010/0280228 A1 | 11/2010 | Snyder | |
| 2012/0192901 A1 | 8/2012 | Cummings | |
| 2012/0202975 A1 | 8/2012 | Cummings | |
| 2013/0323812 A1 | 12/2013 | Cummings | |

FOREIGN PATENT DOCUMENTS

WO    2011/088225 A1    7/2011

OTHER PUBLICATIONS

Fontanals, Nuria et al. "Mixed-mode ion-exchange polymeric sorbents: dual-phase materials that improve selectivity and capacity." Trends in Analytical Chemistry (2010) 29 765-779.*
Tosoh website. "Principles of Ion Exchange Chromatography." accessed by the examiner at <//http://web.archive.org/web/20100227101844/http://www.separations.us.tosohbioscience.com/ServiceSupport/TechSupport/ResourceCenter/PrinciplesofChromatography/IonExchange> on Aug. 19, 2015. Archived by web.archive.org on Feb. 27, 2010.*
Eriksson et al.; "MAb contaminant removal with a multimodal anion exchanger—A platform step to follow Protein A"; *BioProcess International*; 7(2):52-56 (2009).
The International Search Report and Written Opinion from PCT/US2013/025362, dated Apr. 22, 2013.
Ghose et al.; "pH Transitions in ion-exchange systems: Role in the development of a cation-exchange process for a recombinant protein"; *Biotechnology Progress*; 18(3):530-537 (2002).
Lendero et al., "Characterization of ion exchange stationary phases via pH transition profiles," *J. Chromatog. A*; 1185(1):59-70 (Jan. 2008).
The Extended European Search Report from EP Appl. No. EP13748604.9, mailed Oct. 12, 2015.

* cited by examiner

*Primary Examiner* — Christopher A Hixson

(74) *Attorney, Agent, or Firm* — Kilpatrick Townsend & Stockton LLP

(57) ABSTRACT

Provided are methods and compositions for reducing or eliminating pH excursions in cation and anion exchange chromatography.

27 Claims, 3 Drawing Sheets

REDUCING PH EXCURSIONS IN ION EXCHANGE CHROMATOGRAPHY USING DISPLACING COUNTER IONS

CROSS-REFERENCE TO RELATED PATENT APPLICATIONS

The present patent application claims benefit of priority to U.S. Provisional Patent Application No. 61/598,706, filed Feb. 14, 2012, which is incorporated by reference.

BACKGROUND OF THE INVENTION

Transient changes in effluent pH can occur during ion-exchange chromatography. These changes are sometimes referred to as "pH excursions" or "pH transitions" and can be unexpected and uncontrolled. Under some conditions, considerable pH excursions can occur in ion-exchange systems even if the pH of the solution entering the chromatography column is the same as the pH of the column equilibration solution. This phenomenon is described, for example, in Ghose et al., *Biotechnol. Prog.* 18:530-537 (2002). Pabst and Carta, *J. Chromatography A* 1142:19-31 (2007) also describe this phenomenon, noting that uncontrolled pH transitions occur in cation exchange columns during equilibration and salt elution when the stationary phase contains weak acid groups even if the mobile phase is buffered and the buffering species does not interact with the stationary phase.

It has previously been essentially impossible to generate a collinear pH/conductivity gradient in cation exchange chromatography in part due to pH excursions. On cation exchangers, the pH drops as soon as sodium chloride is introduced. Depending on the choice and concentration of buffering species, the charge characteristics of the exchanger, and the concentration of sodium chloride introduced, many column volumes of buffer can be required before pH normalizes. The pH increase will not parallel conductivity, since conductivity rises linearly from the start of the gradient. This causes aberrant elution profiles that can substantially reduce the quality of the fractionation. The corresponding phenomenon is also observed in anion exchange chromatography in which the pH increases initially in an aberrant non-linear fashion in an increasing salt gradient.

The methods described herein address these and other issues.

BRIEF SUMMARY OF THE INVENTION

In one aspect, methods of suppressing formation of uncontrolled pH excursions on a charged solid support having associated hydrogen or hydroxide ions are provided. In some embodiments, the methods comprise: contacting the solid support with a solution comprising displacing counterions with a charge opposite the net charge of the solid support, thereby replacing hydrogen ions associated with a negatively charged solid support, or replacing hydroxide ions associated with a positively charged solid support; and subsequently eluting a target molecule from the solid support, wherein the eluting comprises increasing conductivity of an elution solution in contact with the solid support.

In some embodiments, the methods comprise: contacting the solid support with a solution comprising displacing counterions with a charge opposite the net charge of the solid support, thereby replacing the majority of hydrogen ions associated with a negatively charged solid support, or replacing the majority of hydroxide ions associated with a positively charged solid support; and eluting a target molecule from the solid support, wherein the eluting comprises increasing conductivity of an elution solution in contact with the solid support.

In some embodiments, prior to the contacting, the solid support is in association with: an equilibration buffer; a wash buffer; or a loading buffer. In some embodiments, the solid support is a cation exchange support and the equilibration buffer has a pH from 4 to 7. In some embodiments, the solid support is an anion exchange support and the equilibration buffer has a pH from 6.5 to 9.

In some embodiments, the solid support comprises negative charges and hydrogen ions are associated with the negative charges. In some embodiments, the solid support is a cation-exchange solid support. In some embodiments, the solid support is a mixed mode solid support having cation-exchange functionality. In some embodiments, the mixed mode solid support having cation-exchange functionality further comprises hydrophobic functionality. In some embodiments, the displacing counter ion is a positively-charged molecule selected from an amine, amine derivative, Tris, and histidine. In some embodiments, the displacing counter ion is at a concentration of about 100 to about 500 mM.

In some embodiments, the solid support comprises positive charges and hydroxide ions are associated with the positive charges. In some embodiments, the solid support is a anion-exchange solid support. In some embodiments, the solid support is a mixed mode solid support having anion-exchange functionality. In some embodiments, the mixed mode solid support having anion-exchange functionality further comprises hydrophobic functionality.

In some embodiments, the displacing agent is a negatively-charged molecule selected from glutamate, aspartate, phosphate, and citrate. In some embodiments, the displacing counter ion is at a concentration of about 100 to about 500 mM.

In some embodiments, the eluting further comprises deliberately changing the pH of the elution solution. In some embodiments, the eluting does not substantially change the pH of the elution solution.

In some embodiments, the solid support comprises negative charges associated with hydrogen ions and the eluting further comprises increasing the pH of the elution solution.

In some embodiments, the solid support comprises positive charges associated with hydrogen ions and the eluting further comprises decreasing the pH of the elution solution.

In some embodiments, the solution comprising displacing counter ions further comprises a zwitterionic buffer. In some embodiments, the buffer is a zwitterionic buffer. In some embodiments, the solid support comprises negative charges and the buffer is a negatively-charged buffer. In some embodiments, the solid support comprises positive charges and the buffer is a positively-charged buffer.

In some embodiments, the target molecule is a biomolecule. In some embodiments, the biomolecules is a protein. In some embodiments, the protein is an antibody.

DEFINITIONS

Figure 1:
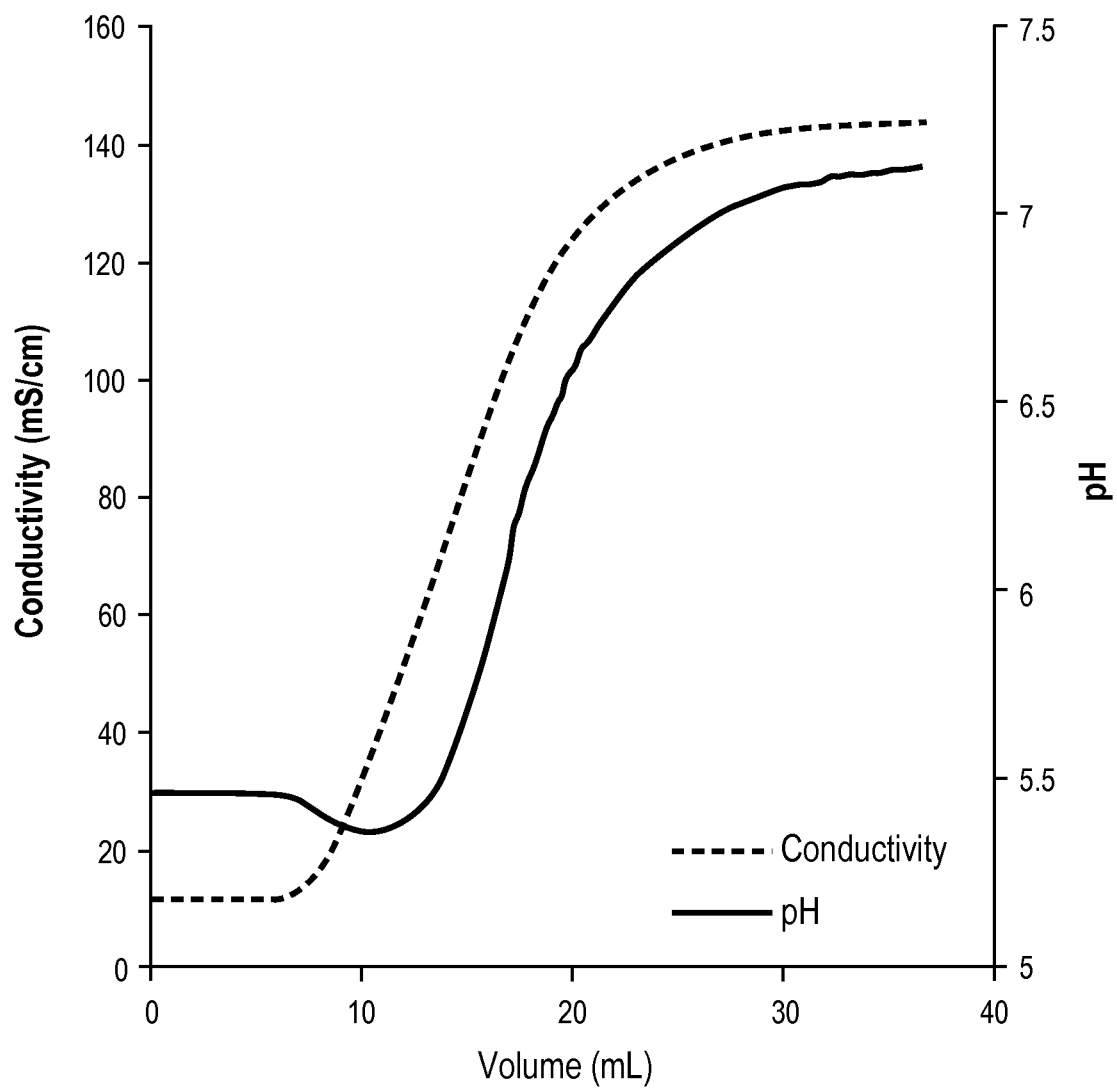
FIG. 1 shows changes or pH and conductivity resulting from the methods of Example 1.

A "counter ion displacing agent" refers to a chemical agent with a charge opposite the net charge of the chromatography media to which it is being applied, wherein the counter ion displaces a hydrogen or hydroxide ion associated with a charged ion exchange solid support. The counter ion displacing agent may be a buffering ion or an ion that is not normally considered to be a buffering ion. For example, in the case of a net negatively charged chromatography support, the counter ion displacing agent may be a cationic buffer such as Tris, imidazole, histidine, or histamine, but may also include cationic species such as lysine or arginine that are not commonly used as buffering agents. The counter ion displacing agent may have a single positive charge (e.g., such as Tris or imidazole), or more than a single positive charge (e.g., such as histamine, histidine, lysine, or arginine). It may also include one or more negative charges, so long as the net charge on the counterion displacing agent (used with the net negatively-charged chromatography support) is positive. The counter ion displacing agent used with the net negatively-charged chromatography support may also include more than two positive charges.

In the case of a net positively-charged chromatography support, the counter ion displacing agent may be an anionic buffer such as acetate, phosphate, citrate, or borate, but may also include anionic species that are not commonly used as buffering agents. The counterion displacing agent may have a single negative charge (e.g., such as acetate), or more than a single negative charge (e.g., such as phosphate or citrate). The counterion displacing agent may also include more than two negative charges. The counterion displacing agent may also include one or more positive charges so long as the net charge on the counterion displacing agent (used with the net positively-charged chromatography support) is negative.

"Antibody" refers to an immunoglobulin, composite, or fragmentary form thereof. The term may include but is not limited to polyclonal or monoclonal antibodies of the classes IgA, IgD, IgE, IgG, and IgM, derived from human or other mammalian cell lines, including natural or genetically modified forms such as humanized, human, single-chain, chimeric, synthetic, recombinant, hybrid, mutated, grafted, and in vitro generated antibodies. "Antibody" may also include composite forms including but not limited to fusion proteins containing an immunoglobulin moiety. "Antibody" may also include antibody fragments such as Fab, F(ab')2, Fv, scFv, Fd, dAb, Fc and other compositions, whether or not they retain antigen-binding function.

"Mixed mode chromatography support" refers to a solid phase chromatographic support that employs multiple chemical mechanisms to adsorb proteins or other solutes. The solid phase can be a porous particle, nonporous particle, membrane, or monolith. Examples include but are not limited to chromatographic supports that exploit combinations of cation exchange (i.e., in which the support is negatively charged) and hydrophobic interaction and chromatographic supports that exploit combinations of anion exchange (i.e., in which the support is positively charged) and hydrophobic interaction.

"Target biomolecule" refers to a biomolecule, or molecule of biological origin, for purification according to the methods of the present invention. Target molecules include, but are not limited to, proteins or nucleic acids (e.g., RNA or DNA). Examples of proteins include but are not limited to antibodies, enzymes, growth regulators, clotting factors, and phosphoproteins.

"Biomolecule preparation" and "biological sample" refer to any composition containing a target molecule of biological origin (a "biomolecule") that is desired to be purified. In some embodiments, the target molecule to be purified is an antibody or non-antibody protein.

DETAILED DESCRIPTION OF THE INVENTION

I. Introduction

Methods for avoiding pH excursions in ion exchange chromatography have been discovered and are described herein. The methods involve displacement of hydrogen ions or hydroxide ions (depending on charge on the solid support) on an ion exchange solid support prior to elution. By displacing the hydrogen ions or hydroxide ions (which cause the pH excursions) before elution, a subsequent elution comprising increasing conductivity (and ionic strength) can proceed without substantial pH excursions.

Displacement of hydrogen ions or hydroxide ions can be achieved using a solution comprising displacing counter ions, i.e., counter ions having the same charge (positive or negative) as the hydrogen ions or hydroxide ions to be displaced. For example, in the case of cation exchangers (i.e., negatively-charged ion exchange solid phase supports) and mixed mode supports having a cation exchange functionality, positively charged hydrogen ions are typically associated with the negative charges on the solid support. The hydrogen ions can be displaced by contacting the solid support with a positively-charged displacing counter ion, thereby washing the majority of the hydrogen ions free from the solid support prior to elution. In situations in which anion exchangers are employed, the solid support will be associated with hydroxide ions and these can be displaced by a negatively-charged displacing counter ion. In either case (cation or anion exchange), because the counter ion has replaced the pH-changing ion (hydrogen or hydroxide ion, respectively) that would otherwise be released to create uncontrolled pH excursions, subsequent elution conditions involving increased conductivity do not result in substantial pH excursions. In contrast, if an initial displacement counter ion is not used as described above, significant (potentially by 2 pH units or more) pH excursions are observed. By improving pH control as described herein, it is possible to form conductivity gradients relatively free from aberrant pH excursions. This applies to situations where the aim is to perform a conductivity gradient at constant pH, or to situations where the aim is to perform a conductivity gradient coincident with a controlled change of pH, including where the pH increases coincident with conductivity, or decreases.

II. Methods

The methods provided herein generally provide for at least two steps: (1) a hydrogen ion or hydroxide ion displacement step and (2) a subsequent elution of a target molecule. In some embodiments, the ion displacement step comprises contacting the solid support with a displacing counter ion in the presence of an appropriate buffer, such that hydrogen or hydroxide ions released by the displacing counter ion are neutralized prior to elution. It will be appreciated that additional steps can be performed before, during and between these two steps. By providing the initial displacement solution, a subsequent elution involving increased conductivity will not result in pH excursions. Significant pH excursions that would otherwise occur can include, e.g., those in which chromatography output solutions have more than 0.1, 0.2, 0.3, 0.5, 0.75, 0.9, 1, 1.5, or 2 pH units different from input solutions.

A. Hydrogen Ion or Hydroxide Ion Displacement

As noted above, chromatography solid supports having cation exchange functionality typically have significant amounts of hydrogen ions associated with the negatively-charged supports. Similarly, chromatography solid supports having anion exchange functionality typically have significant amounts of hydroxide ions associated with the positively-charged supports. The methods described herein substantially displace the hydrogen or hydroxide ions with a counter ion that does not substantially affect pH of the solution in contact with the solid support. In some embodiments, the counter ion has a greater affinity for the solid support than the hydrogen ion or the hydroxide ion. While the principle is the same, for purposes of explanation, cation exchange and anion exchange functionalities are described separately below. By providing the initial hydrogen ion displacement buffer (or hydroxide ion displacement buffer when using anion exchange), it will be possible to maintain relatively greater pH control through the course of the conductivity gradient.

In the case where the solid support has a cation exchange functionality, positively charged hydrogen ions are associated with the support. To displace the hydrogen ions, the displacement counter ion is also positively charged so as to compete with the hydrogen ions for binding to the solid support. In some embodiments, the displacement counter ion can be a cationic buffer. Exemplary cationic buffers include, e.g., Tris, imidazole, histidine, or histamine. Other possible cation displacement counter ions can include agents not typically considered buffers. Examples, include but are not limited to, lysine or arginine. As is clear from the counter ions listed above, the displacement counter ion can have a single positive charge (e.g., such as Tris or imidazole), or more than a single positive charge (e.g., such as histamine, histidine, lysine, or arginine). In some embodiments, the counter ion used with cation exchange functionalities can include one or more negative charges, so long as the net charge on the ion is positive. The counter ion displacing agent may also include more than two positive charges. For example, spermidine, or polycations (e.g., polyethyleneimine) can be employed as hydrogen ion-displacing counter ions.

The concentration of the hydrogen ion displacing counter ion can vary. In some embodiments, the concentration of the displacing counter ion is, e.g., between 5-1000 mM e.g., 5-500 mM, 50-300 mM, 200-400 mM, 100-200 mM, etc. Other concentrations can be determined based on the particular solid support and counter ion used. For example, in embodiments in which the counter ions are polyions (having more than one charge per molecule), the concentration of the counter ions can often be lower. In some embodiments, polyionic counter ions are at a concentration of, e.g., 0.1-10%, or 0.5-5%, or 1-3%.

Displacement of the majority or more of the associated hydrogen ions or hydroxide ions can be determined, for example, by the elimination or substantial reduction of a pH excursion. For example, following displacement of the hydrogen or hydroxide ions, the pH of the effluent from the solid support should be substantially the same as the input solution under increasing conductivity conditions. Thus, in some embodiments, under increasing conductivity conditions (a gradient or stepwise elution for example) input and effluent does not differ by more than, e.g., 0.1, 0.2, 0.3, 0.5, 0.75, 0.9, 1, 1.5, or 2 pH units.

The solution comprising the hydrogen ion displacing counter ion can be adjusted to any pH. However, in many embodiments, the pH of the solution comprising the displacing counter ion will be below pH 7, and some times below pH 6 or 5 or even 4. For example, in some embodiments, the solution comprising the displacing counter ion has a pH of between 4-7.

In the case where the solid support has an anion exchange functionality, negatively charged hydroxide ions are associated with the support. To displace the hydroxide ions, the displacement counter ion is also negatively charged so as to compete with the hydroxide ions for binding to the solid support. In some embodiments, the displacement counter ion can be an anionic buffer. Exemplary anionic buffers include, e.g., acetate, phosphate, citrate, formate, succinate, malate, or lactate. Other possible anion displacement counter ions can include agents not typically considered buffers, such as glutamate or aspartate. In some embodiments, the counter ion used with anion exchange functionalities can include one or more positive charges, so long as the net charge on the ion is negative (examples include, e.g., glutamate and aspartate).

The counter ion displacing agent may also include more than two negative charges. For example alginic acid, carageenan, caboxymethyl cellulose, or carboxymethyl dextran can be employed as hydroxide ion-displacing counterions. Use of this last category will lower the concentration needed to achieve the same displacement. Because of their size, they embody much more displacing ability per mole. Thus, for example, while 300 mM acetate may displace a certain amount of hydroxide ions, only 10-50 mM alginic acid may produce the same displacement of hydrogen ions.

The concentration of the hydroxide ion displacing counter ion can vary. In some embodiments, the concentration of the displacing counter ion is, e.g., between 100-500 mM, e.g., 200-400 mM, etc. Other concentrations can be determined based on the particular solid support and counter ion used.

Applications on solid phases with anion exchange functionalities will generally begin at high pH. They may elute towards lower pH. In some embodiments, the solid phase is equilibrated to a pH of 6.5-8.5. A pre-elution treatment with an anionic counter ion displacing agent removes most of the hydroxide ions that were accumulated during column equilibration and prevents an uncontrolled positive pH excursion. In some embodiments, the operating pH is in the range of 6-8, but may range from 4-9 or greater.

In some embodiments, the solution comprising the displacing counter ion also comprises a buffer (or a second buffer in the case where the displacing counter ion itself is also a buffer). In some embodiments, the buffer is a zwitterionic buffer. Exemplary zwitterionic buffers include, but are not limited to, MES or HEPES. The buffer can act to maintain the pH of the solution and is generally, but not always, at a lower concentration than the concentration of the displacing counter ion. In some embodiments, the zwitterionic buffer is at a concentration of 20-50 mM. In some embodiments, the buffer is at a concentration between 1/20 and 1/5 of the molar concentration of the displacing counter ion. For example, in some embodiments, the displacing counter ion is at a concentration of about 300 mM and the buffer is at a concentration of about 30 mM.

The use of multiple buffering species can be helpful, for example, to generate a linear pH gradient with a span greater than 1 pH unit. For example two buffering components can be selected such that one has a pKa no higher 0.5 pH units above the lowest pH in the gradient, and the other buffer has a pKa no higher than 0.5 pH units below the highest pH in the gradient. In addition, in some embodiments, the maximum practical interval between buffer pKas is no greater than 1 pH unit. Consistent with this approach, if the span of the pH interval is 3 pH units, three or more buffering species can be used. In cases where a buffer has multiple pKas, a simple buffer can function as multiple buffering species. In some embodiments, the buffers used to create the pH gradient (aside, for example, from the displacing counter ion used to displace hydrogen or hydroxide ions) are all of one ion type, for example, all zwitterionic.

As noted above, the displacing counter ion step can be preceded by other steps. In some embodiments, before the displacing counter ion step, the chemical environment surrounding the solid support is equilibrated. In some embodiments, the mixed mode support can be equilibrated to establish the appropriate pH, conductivity, and/or concentration of salts. Equilibration of the support is accomplished, for example, by flowing an equilibration buffer containing appropriate reagents across the solid support (e.g., through the column). Equilibration buffering agents may include, but are not limited to, MES, HEPES, BICINE, imidazole, and Tris. For example, in some embodiments, the buffering agent is the same as the (e.g., zwitterionic) buffer in the above-described solution. In some embodiments, the equilibration solution will comprise at least some salt (e.g., sodium chloride at 10, 50, 100 mM, etc.). In some embodiments, the pH of the equilibration solution will be substantially the same as the pH of the counter ion displacement solution.

B. Elution

Following the displacement of the hydrogen or hydroxide ions on the solid support, the target molecule can be eluted. As noted above, elution can occur immediately after the displacement or intervening steps can occur prior to elution. However, to benefit from the displacement step, the intervening steps should not result in association of a substantial amount of hydrogen ions or hydroxide ions on the solid support.

Elution will comprise an increase in conductivity (ionic strength) in the solution in contact with the solid support (e.g., with or without a change of pH as part of the elution process). The elution can involve, for example, a conductivity gradient, one or more stepwise increases in conductivity, etc. In addition, if desired, the pH of the elution solution can be changed (increased or decreased compared to the equilibration conditions, for example). In some embodiments, the elution buffer contains electroneutral (nonionic or zwitterionic) modifiers to modulate hydrogen bonds and/or hydrophobic interactions (urea, nonionic surfactants, zwitterionic surfactants, glycols, alcohols).

In initial development of an elution procedure, it may be helpful to run one or more conductivity and/or pH gradients to determine optimal elution conditions. Subsequently it may be more convenient and efficient to run a step gradient at the optimal elution condition.

C. Optional Additional Steps

The present invention may be combined with other purification methods to achieve higher levels of purification. Examples include, but are not limited to, other methods commonly used for purification of biomolecules, such as protein A (when purifying antibodies) and other forms of affinity chromatography, anion exchange chromatography, apatite chromatography (e.g., hydroxyapatite and fluorapatite), cation exchange chromatography, hydrophobic interaction chromatography, immobilized metal affinity chromatography, and additional mixed mode chromatography methods. Other options, include, but are not limited to precipitation, crystallization, and/or liquid partitioning methods.

D. Exemplary Ion Exchange and Mixed Mode Solid Supports

Generally, any ion exchange or non-apatite mixed mode solid phase having ion exchange functionality is expected to function in the methods described above.

In some embodiments, the solid phase comprises cation exchange functionality. Cation exchange moieties are negatively charged and are selective for positively charged polypeptide biomolecules. Depending on the charge characteristics desired, an appropriate cation exchange moiety can be selected by one skilled in the art. Non-limiting examples of cation exchange moieties include carboxy, sulfo, and phospho moieties. Exemplary cation exchange moieties are described in, e.g., US Patent Publication No. US2009/0270596. Exemplary commercially-available cation exchange supports include, but are not limited to, UNOsphere S™ (Bio-Rad Laboratories), Capto S™ (GE Healthcare), Fractogel SE Hicap™ (M) (Merck KGaA), CM Ceramic HyperD™ (PALL).

One group of exemplary mixed mode supports includes a cation exchange functionality that may be augmented by additional chemical features that endow with the ability to participate in one or more of the following types of interactions anion exchange, hydrophobic interaction, hydrophilic interaction, hydrogen bonding, pi-pi bonding, and metal affinity. Exemplary commercially-available mixed mode supports with cation exchange functionality include, but are not limited to, Capto MMC™ (GE Healthcare) and Nuvia™ cPrime™ (Bio-Rad Laboratories).

In some embodiments, the solid phase comprises anion exchange functionality. Anion exchange moieties are negatively charged and are selective for negatively-charged polypeptides biomolecules. Depending on the charge characteristics desired, an appropriate anion exchange moiety can be selected by one skilled in the art. Non-limiting examples of anion exchange moieties include diethylaminoethyl, diethylmethylaminoethyl, diethyl-[2-hydroxypropyl]aminoethyl, allylamine quaternary ammonium, polyallylamine, polyethyleneimine, pyridine and pyridyl derivative moieties. Exemplary commercially-available mixed mode supports having anion exchange functionality include, but are not limited to, UNOsphere Q™, Capto Q™, Fractogel TMAE and Q Ceramic HyperD™.

Another group of exemplary mixed mode supports that include an anion exchange functionality that may be augmented by additional chemical features that endow with the ability to participate in one or more of the following types of interactions cation exchange, hydrophobic interaction, hydrophilic interaction, hydrogen bonding, pi-pi bonding, and metal affinity. An exemplary commercially-available anion exchange support is Capto Adhere™ (GE Healthcare).

IV. Target Biomolecules

The present invention provides methods of purifying a target biomolecule from a biological sample under bind-elute conditions. Target biomolecules can include any biological molecule that can be purified using ion exchange chromatography. Examples of target biomolecules include, but are not limited to, proteins (e.g., antibodies, non-antibody therapeutic proteins, enzymes, growth regulators, and clotting factors).

In some embodiments, the target molecule is an antibody or antibody fragment. In some embodiments, the antibody is an IgG, IgM, IgA, IgD, or IgE. In some embodiments, the target biomolecule is a Fc-fusion protein. Antibody preparations for use in the present invention can include unpurified or partially purified antibodies from natural, synthetic, or recombinant sources. Unpurified antibody preparations may come from various sources including, but not limited to, plasma, serum, ascites fluid, milk, plant extracts, bacterial lysates, yeast lysates, or conditioned cell culture media. Partially purified preparations may come from unpurified preparations that have been processed by at least one chromatography, precipitation, other fractionation step, or any combination of the foregoing.

Any antibody preparation can be used in the methods described herein, including unpurified or partially purified antibodies from natural, synthetic, or recombinant sources. Unpurified antibody preparations can come from various sources including, but not limited to, plasma, serum, ascites, milk, plant extracts, bacterial lysates, yeast lysates, or conditioned cell culture media. Partially purified preparations can come from unpurified preparations that have been processed by at least one chromatography, precipitation, other fractionation step, or any combination of the foregoing. In some embodiments, the antibodies have not been purified by protein A affinity prior to purification.

EXAMPLES

Example 1

A Nuvia™ cPrime™ (Bio-Rad) column comprising the ligand p-aminohippuric acid attached to a large pore matrix produced by polymerization of monomers 3-allyloxy-1,2-propanediol, vinylpyrrolidinone and crosslinked with N,N'-methylenebisacrylamide was equilibrated with 50 mM MES, 100 mM NaCl, pH 6.0. An antibody sample was loaded at pH about 6 with conductivity about physiological levels (about 12 mS/cm). The column is washed with two column volumes (CV) equilibration buffer. Hydrogen ions were replaced by re-equilibrating the chromatography support with 30 mM MES, 300 mM Tris, adjusted to pH 5.5 with acetic acid, thereby replacing hydrogen ions on the surface of the column with Tris ions. Elution was initiated with a 10CV linear gradient to 100 mM Hepes, 2 M NaCl. See, FIG. 1. Because the hydrogen ions have been eliminated, pH does not decrease when NaCl is introduced, and pH increases linearly with conductivity.

Example 2

Figure 2:
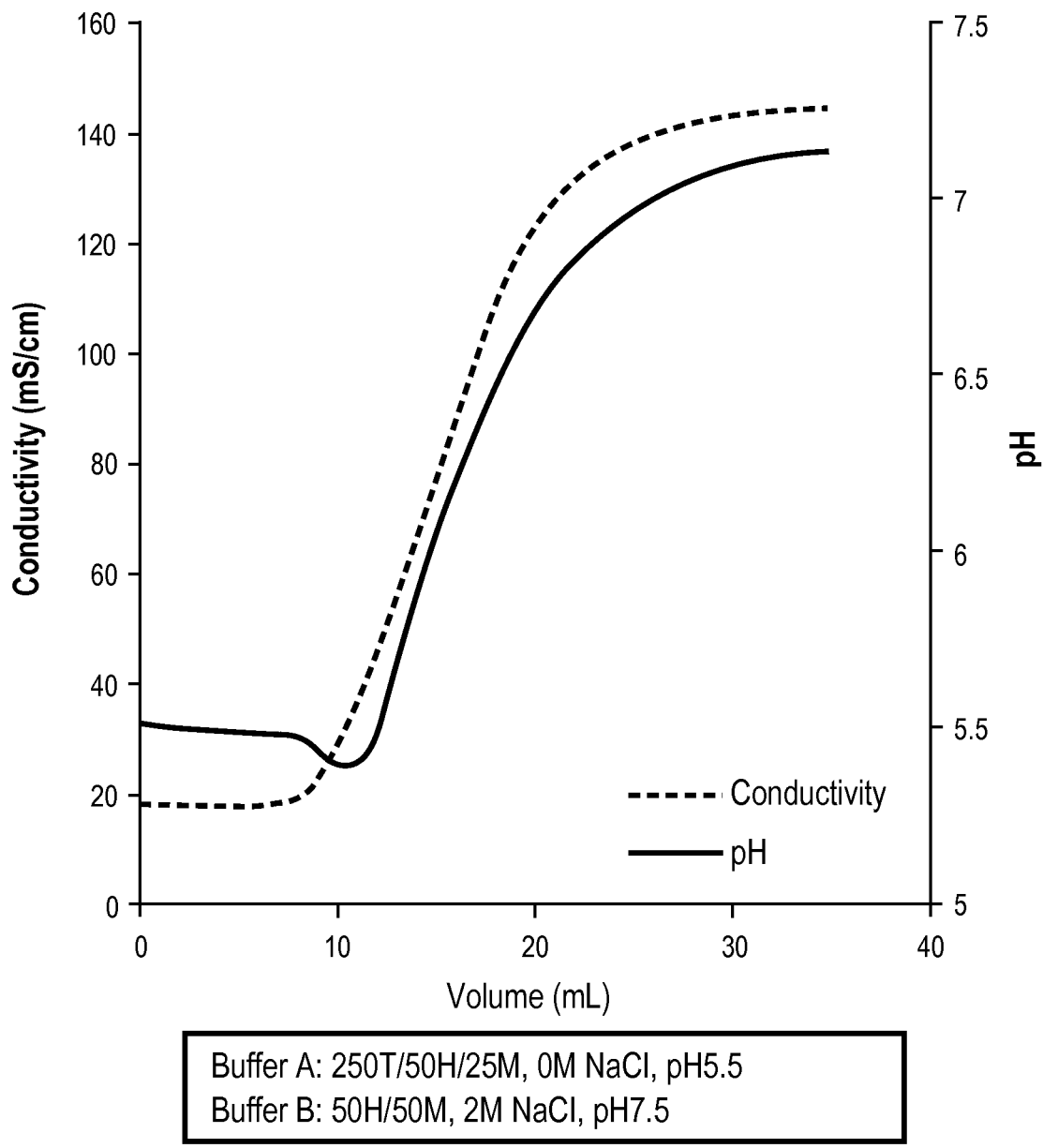
FIG. 2 shows changes or pH and conductivity resulting from the methods of Example 2.

A Nuvia™ cPrime™ (Bio-Rad) column comprising the ligand p-aminohippuric acid attached to a large pore matrix produced by polymerization of monomers 3-allyloxy-1,2-propanediol, vinylpyrrolidinone and crosslinked with N,N'-methylenebisacrylamide was equilibrated with 250 mM Tris, 50 mM HEPES, 25 mM MES, titrated with acetic acid to pH 5.5 (conductivity about 12 mS/cm). A linear gradient was formed by proportionally mixing the gradient-start buffer above with a gradient-end buffer formulated as 50 mM MES, 50 mM HEPES, 2 M NaCl, pH 7.5. This resulted in an initial descending pH excursion of about 0.07 pH units and restoration of the initial pH in about 2.5 column volumes, after which the pH and conductivity ascended in parallel. See, FIG. 2. The amplitude and duration of the pH excursion can be eliminated by increasing the concentration of Tris. See, Example 3. As raising Tris concentration raises conductivity, consideration should be given to the ability of the particular target molecule to tolerate increased conductivity.

Example 3

Figure 3:
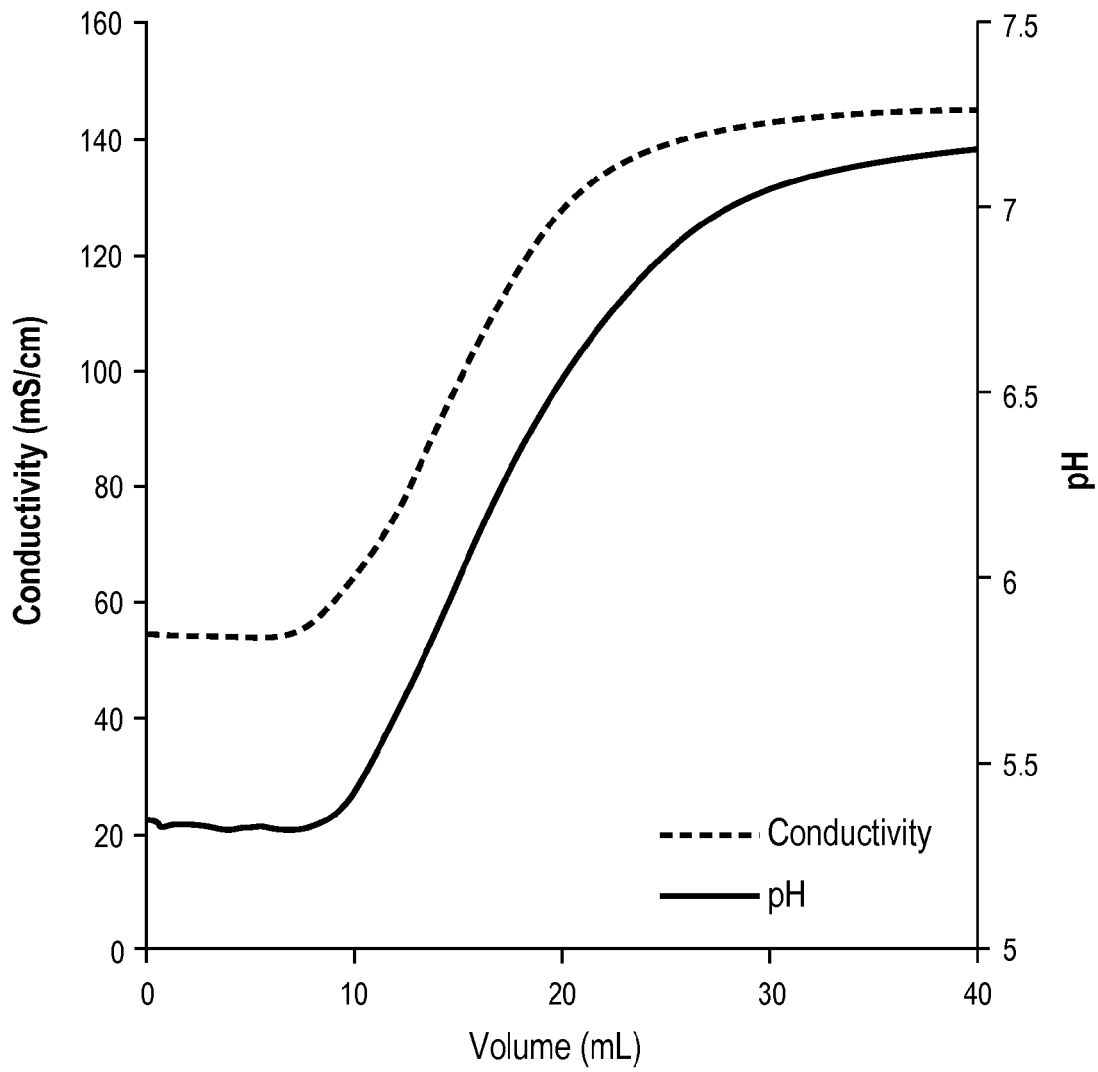
FIG. 3 shows changes or pH and conductivity resulting from the methods of Example 3.

A Nuvia™ cPrime™ (Bio-Rad) column comprising the ligand p-aminohippuric acid attached to a large pore matrix produced by polymerization of monomers 3-allyloxy-1,2-propanediol, vinylpyrrolidinone and crosslinked with N,N'-methylenebisacrylamide was equilibrated with 1000 mM Tris, 50 mM MES, 50 mM HEPES titrated to pH 5.5. A linear gradient was formed by proportionally mixing the gradient-start buffer above with a gradient-end buffer formulated as 50 mM MES, 50 mM HEPES, 2 M NaCl, pH 7.5. This resulted in essentially no descending pH excursion and essentially parallel rise in the pH and conductivity. See, FIG. 3.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of suppressing formation of pH excursions on a charged solid support having associated hydrogen or hydroxide ions, the method comprising
   providing a solid support in association with an equilibration buffer, a wash buffer, or a loading buffer and subsequently;
   contacting the solid support with a solution comprising displacing counter ions with a charge opposite the net charge of the solid support, wherein the displacing counter ion is a positively-charged molecule thereby replacing hydrogen ions associated with a negatively charged solid support, or wherein the displacing counter ion is a negatively-charge molecule thereby replacing hydroxide ions associated with a positively charged solid support; and subsequently
   eluting a target molecule from the solid support, wherein the eluting comprises increasing conductivity of an elution solution in contact with the solid support.

2. The method of claim 1, wherein the solid support is a cation exchange support and the equilibration buffer has a pH from 4 to 7.

3. The method of claim 1, wherein the solid support is an anion exchange support and the equilibration buffer has a pH from 6.5 to 9.

4. The method of claim 1, wherein the solid support comprises negative charges and hydrogen ions are associated with the negative charges.

5. The method of claim 4, wherein the solid support is a cation-exchange solid support.

6. The method of claim 4, wherein the solid support is a mixed mode solid support having cation-exchange functionality.

7. The method of claim 6, wherein the mixed mode solid support having cation-exchange functionality further comprises hydrophobic functionality.

8. The method of claim 5, wherein the displacing counter ion is a positively-charged molecule selected from an amine, amine derivative, Tris, and histidine.

9. The method of claim 5, wherein the displacing counter ion is at a concentration of about 100 to about 500 mM.

10. The method of claim 1, wherein the solid support comprises positive charges and hydroxide ions are associated with the positive charges.

11. The method of claim 10, wherein the solid support is an anion-exchange solid support.

12. The method of claim 10, wherein the solid support is a mixed mode solid support having anion-exchange functionality.

13. The method of claim 12, wherein the mixed mode solid support having anion-exchange functionality further comprises hydrophobic functionality.

14. The method of claim 10, wherein the displacing agent is a negatively-charged molecule selected from glutamate, aspartate, phosphate, and citrate.

15. The method of claim 14, wherein the displacing counter ion is at a concentration of about 100 to about 500 mM.

16. The method of claim 1, wherein the eluting further comprises changing the pH of the elution solution.

17. The method of claim 1, wherein the eluting does not substantially change the pH of the elution solution.

18. The method of claim 1, wherein the solid support comprises negative charges associated with hydrogen ions and the eluting further comprises increasing the pH of the elution solution.

19. The method of claim 1, wherein the solid support comprises positive charges associated with hydroxide ions and the eluting further comprises decreasing the pH of the elution solution.

20. The method of claim 1, wherein the solution comprising displacing counter ions further comprises a buffer.

21. The method of claim 20, wherein the buffer is a zwitterionic buffer.

22. The method of claim 21, wherein the solid support comprises negative charges and the buffer is a negatively-charged buffer.

23. The method of claim 21, wherein the solid support comprises positive charges and the buffer is a positively-charged buffer.

24. The method of claim 1, wherein the target molecule is a biomolecule.

25. The method of claim 24, wherein the biomolecule is a protein.

26. The method of claim 25, wherein the protein is an antibody.

27. The method of claim 1, wherein the positively-charged molecule is a buffering ion.

* * * * *